United States Patent [19]
McCullough

[11] 3,994,635
[45] Nov. 30, 1976

[54] SCROLL MEMBER AND SCROLL-TYPE APPARATUS INCORPORATING THE SAME

[75] Inventor: John E. McCullough, Carlisle, Mass.

[73] Assignee: Arthur D. Little, Inc., Cambridge, Mass.

[22] Filed: Apr. 21, 1975

[21] Appl. No.: 570,170

[52] U.S. Cl. .................................. 418/55; 418/57
[51] Int. Cl.² ................... F01C 1/02; F04C 17/02; F01C 19/00
[58] Field of Search ............. 418/55, 56, 57, 125, 418/129, 142, 144

[56] References Cited
UNITED STATES PATENTS

| | | | |
|---|---|---|---|
| 801,182 | 10/1905 | Creux | 418/55 |
| 1,041,721 | 10/1912 | Ball | 418/55 |
| 1,376,291 | 4/1921 | Rolkerr | 418/55 |
| 1,766,005 | 6/1930 | Sullivan | 418/83 |
| 3,506,275 | 4/1970 | Moriyama | 418/142 |
| 3,600,114 | 8/1971 | Dvorak et al. | 418/55 |
| 3,718,412 | 2/1973 | McCormick | 418/142 |
| 3,827,701 | 8/1974 | Sakamaki | 418/142 |
| 3,874,827 | 4/1975 | Young | 418/55 |

*Primary Examiner*—John J. Vrablik
*Attorney, Agent, or Firm*—Bessie A. Lepper

[57] ABSTRACT

A scroll member is provided for use in scroll-type apparatus. It is formed of a separate end plate having an involutely configured groove in the face thereof and a separate involute wrap which is seated in the groove. The seating of the wrap in the groove may be such as to permit it to undergo small axial and radial excursions within the groove to impart compliance/sealing characteristics to the scroll member. Alternatively, the wrap may be rigidly mounted in the groove and, if desired, separate compliance/sealing means provided for the wrap. The construction of scroll members according to this invention achieves a marked decrease in cost of the scroll members and of scroll-type apparatus incorporating them.

26 Claims, 29 Drawing Figures

SCROLL MEMBER AND SCROLL-TYPE APPARATUS INCORPORATING THE SAME

This invention relates to scroll-type apparatus and more particularly to the construction of the scroll members used therein and to scroll-type apparatus incorporating the scroll members so constructed.

There is known in the art a class of devices generally referred to as "scroll" pumps, compressor and engines wherein two interfitting spiroidal or involute spiral wrap elements of like pitch are mounted on separate end plates. These spirals are angularly and radially offset to contact one another along at least one pair, and generally several pairs, of line contacts such as between spiral curved surfaces. A pair of line contacts will lie approximately upon one diameter drawn through the central region of the scrolls. The fluid volume so formed therefore extends all the way around the central region of the scrolls. In certain special cases the pocket or fluid volume will not extend the full 360°, but because of special porting arrangements will subtend a smaller angle about the central region of the scrolls. The pockets define fluid volumes, the angular position of which varies with relative orbiting of the spiral centers; and all pockets maintain the same relative angular position. As the contact lines shift along the scroll surfaces, the pockets thus formed experience a change in volume. The resulting zones of lowest and highest pressures are connected to fluid ports.

An early patent to Creux (U.S. Pat. No. 801,182) describes this general type of device. Among subsequent patents which have disclosed scroll compressors and pumps are U.S. Pat. Nos. 1,376,291, 2,475,247, 2,494,100, 2,809,779, 2,841,089, 3,560,119, 3,600,114, 3,802,809 and 3,817,664 and British Patent 486,192.

In constructing the scroll members, each of which comprises an end plate with the involute spiral wrap elements attached thereto, it has been the practice to form these scroll members from a single piece of metal by machining out the involute spiral wraps. Although this is, of course, within the capabilities of present milling techniques it consumes a great deal of time and energy and produces large quantities of waste metal. Thus it has been expensive to make the necessary scroll members for scroll-type apparatus, a fact which for many applications does not permit scroll-type apparatus to compete in price with other types of compressors or expansion engines. Such added cost thus outweighs the operational advantages inherent in scroll-type machinery. Moreover, once the scroll members are fabricated by milling out the involute wraps, it is necessary to lap these elements to achieve a desired degree of fit between adjacent scrolls.

Lapping of the two involute spiroidal wraps on the orbiting and stationary scroll members is necessary to minimize wear and maximize the effectiveness of any tangential sealing means used. The problem of attaining satisfactory sealing of the moving fluid pockets is not, however, limited to tangential sealing along the moving line contacts between the wraps, for radial sealing between the end of each involute wrap and the contacting surface of the end plate of the opposing scroll member is at least as important as achieving effective tangential sealing through effective radial contact forces. This fact in turn means that in the absence of any axial compliance/sealing means or similar mechanism, it is also necessary to machine the top of the involute wraps and the surfaces of the end plates to very close tolerances to attain satisfactory radial sealing through effective axial contacting forces. This, too, adds to the expense of making the scroll members; but is not, however, the most satisfactory solution to the radial sealing problem. Moreover, as will be shown below, factors such as a thermal gradient within the apparatus and uneven wear can destroy the effectiveness of the initial close tolerance machining of the axial contacting surfaces.

Several solutions to those radial sealing problems on which the construction of the scroll member has significant bearing have been proposed. In one such solution, radial sealing has been sought to be achieved through the use of one or more mechanical axial constraints, e.g., bolts to force the surfaces into contact (U.S. Pat. No. 3,011,694) requiring precise adjustment to attain efficient radial sealing without undue wearing. If, however, during extended operation of such devices this adjustment is disarranged by one component's experiencing more wear, or by any other mechanism, the problem of wear of other components may grow progressively worse until satisfactory axial contacting is no longer obtained and radial sealing becomes inefficient.

Since the use of surfaces machined to close tolerances and the use of mechanical constraints such as bolts to force axial contacts have not been found to be suitable techniques for achieving radial sealing in commercially produced scroll apparatus, more recent techniques for achieving effective radial sealing have included the use of a compliant fixed scroll member or the use of a pressurized fluid (with or without springs to provide an augmenting axial force) to urge the scroll members into axial contact.

In the case of the use of a compliant fixed scroll member, radial sealing is accomplished by using a fixed scroll member which is capable of undergoing very small excursions in the axial direction and which has some fluid and/or mechanical spring force-applying means associated with it. (Such a scroll-type apparatus is described in Ser. No. 408,287, filed in the name of Niels O. Young, now U.S. Pat. No. 3,874,327). In the use of pressurized fluid (generally in combination with some form a mechanical spring) to achieve radial sealing, the fluid under pressure is used to axially urge the orbiting scroll member in contact with the fixed scroll member. This fluid may be drawn from one of the moving fluid pockets defined within the apparatus (U.S. Pat. Nos. 3,600,114 and 3,817,664 and application Ser. No. 368,907 filed June 11, 1973, in the names of Niels O. Young and John E. McCullough, now U.S. Pat. No. 3,884,599 and assigned to the same assignee as this application) or from an external source. In an application filed in the name of Robert W. Shaffer, Ser. No. 561,479 there is disclosed an improved axial loading means particularly suited for scroll-type compressors and expanders operating at high pressures. In the scroll-type apparatus using these improved axial loading means all of the forces required to achieve efficient axial load carrying are pneumatic forces provided by pressurizing all or a selected portion of the apparatus housing. Thus the housing defines with a surface of the orbiting scroll member a pressurizable chamber whereby the fluid pressure within the chamber forces the orbiting scroll member into continued axial contact relationship with the fixed scroll member. This pressurizable chamber, which is isolated from the fluid pockets defined within the scroll members, may comprise essentially all of the internal volume of the housing or it may constitute less than the entire housing volume.

The substitution of a compliant fixed scroll member with axial forces applied thereto or of pneumatic forces acting upon the orbiting scroll for the use of bolts to force surface contacts have gone a long way to the solving of the radial sealing problems in scroll-type apparatus. However, these techniques still require very accurate machining of both the contacting surfaces, i.e., the surfaces of the end plates and the surfaces of the involute spiral wrap members. As noted above, this requirement of accurate machining adds materially to the cost of the manufacture of scroll type apparatus. Moreover, any axial misalignment in the apparatus during operation will generally result in uneven wear, thus defeating the attainment of the accurate machining. Finally, radial temperature gradients within the apparatus give rise to uneven dimensional changes in the height of the involute wraps.

In an application Ser. No. 561,479 filed in the names of John E. McCullough and Robert W. Schaffer the requirement for close tolerance machining has been eliminated or materially reduced by the providing of axial compliance/sealing means which are associated with the involute wraps and which are used in conjunction with axial contacting means which provide some axial forces to urge the wrap mounted sealing involute and end plate surfaces into sealing contact. These axial compliance/sealing means comprise seal elements generally involutely configured to have the same configuration as the wrap members with which they are used and means to actuate the seal elements by urging them into contact, with a predetermined preload, with the opposing scroll member end plate. These axial compliance/sealing means are particularly suitable for use in scroll apparatus wherein the wraps are relatively thick, e.g. at least about 0.25 inch, and can be machined to have a groove or a central narrow extension member for cooperating with the seal element. Although the use of these axial compliance/sealing means reduces the costs incurred in the close tolerance machining of the top surfaces of the wraps and offers other operational advantages, it does not solve the problem of lowering the cost of the initial formation of the scroll member.

It would therefore be desirable to have a scroll member which could be made in a manner to materially reduce the cost of its manufacture while at the same time requiring that the contacting surfaces used to attain efficient radial sealing need be machined only to conventional accuracy.

It is therefore a primary object of this invention to provide a scroll member, suitable for use in a scroll-type apparatus, which can be made at a cost so that the scroll apparatus in which it is used is competitive with other types of compressors, expansion engines and pumps, thus permitting scroll-type apparatus to be used in a much wider range of applications than heretofore possible. It is another object of this invention to provide a scroll member of the character described which requires machining of both the sides and ends of the involute wraps to only conventional tolerances. Yet another object is to provide a scroll member which may be constructed to provide axial compliance/sealing means inherent in its construction without the necessity for adding such means to the involute wrap. A further object is to provide a scroll member with inherent compliance/sealing means which is capable of maintaining the integrity of any tangential sealing means used. It is yet a further object to provide a scroll member which permits flexibility in the choice of material from which the end plate and involute wrap may be formed since they may be formed of different materials.

Another primary object of this invention is to provide scroll-type apparatus which may be constructed at a cost to make it competitive with other types of similar apparatus, i.e., rotary or positive displacement compressors, expansion engines and pumps. An additional object is to provide scroll-type apparatus of the character described in which the involute wraps may be seated in the end plates to provide axial compliance/sealing characteristics which make it possible to attain efficient radial sealing using conventional machining. Still another object is to provide scroll-type machinery in which effective radial sealing may be insured through the construction of the scroll member while at the same time maintaining the integrity of any tangential sealing means used.

Other objects of the invention will in part be obvious and will in part be apparent hereinafter.

The invention accordingly comprises the features of construction, combinations of elements, and arrangement of parts which will be exemplified in the constructions hereinafter set forth, and the scope of the invention will be indicated in the claims.

According to one aspect of this invention there is provided a unique scroll member suitable for use in scroll-type apparatus in conjunction with a complementary scroll member to define, through the use of axial and radial sealing means, moving fluid pockets and zones of different fluid pressure. This unique scroll member comprises an end plate having defined on the one of its surfaces serving as one of the boundaries for the fluid pockets an involutely configured groove and a separate wrap member having a radial sealing surface and being involutely configured to conform to the configuration of the end plate groove and seated therein. The seating of the involute wrap in the end plate groove may be of a nature to provide inherent axial compliance/sealing properties to the wrap or it may be of a rigid nature in which case axial compliance/sealing means may, if desired, be incorporated into the wrap outer edge as an additional element.

According to another aspect of this invention there are provided a pair of complementary scroll members each formed in accordance with the teaching of this invention and each possessing axial compliance/sealing characteristics designed to ensure efficient radial sealing and to maintain the tangential sealing characteristics imparted to the scroll apparatus, in which the pair of scroll members are used, by suitably radial compliance means.

According to yet another aspect of this invention there is provided improved scroll-type machinery incorporating these unique scroll members. This scroll-type machinery includes radial and tangential sealing means, and in preferred embodiments there are included axial compliance/sealing means (whether inherent in the scroll member construction or provided as an additional element) which make it possible to construct the scroll members using only conventional machining techniques while retaining the integrity of any tangential sealing means used.

For a fuller understanding of the nature and objects of the invention, reference should be had to the following detailed description taken in connection with the accompanying drawings in which.

Figure 1:
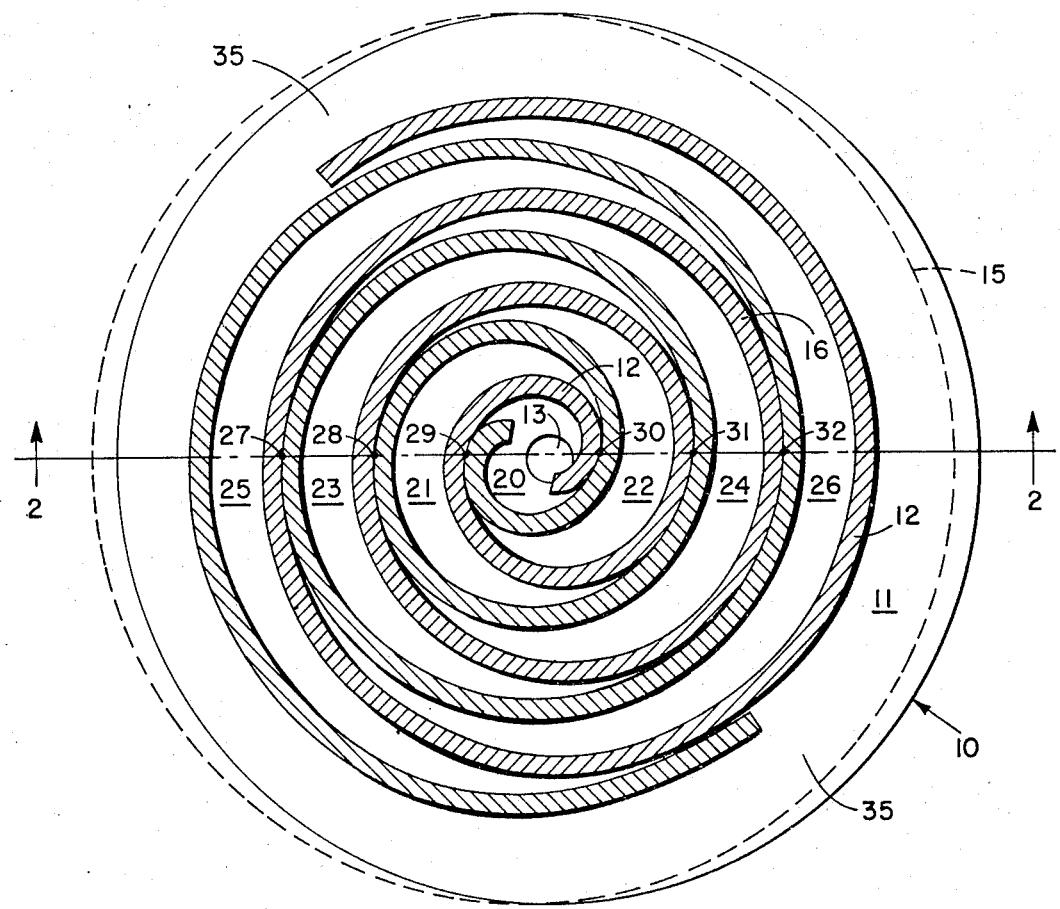
FIG. 1 is a cross section through the involute wrap members of a typical scroll-type apparatus.

Inasmuch as radial sealing within scroll-type apparatus is an essential feature of such apparatus, and further since any scroll member construction and any additional axial compliance/sealing means must be capable of attaining radial sealing and of maintaining the integrity of the tangential sealing mechanism, it will be helpful, before describing the scroll member of this invention to briefly review the problems of radial and tangential sealing to understand the role which the construction of the scroll members must play in effectively sealing off the pockets within the apparatus.

In the design and construction of scroll-type apparatus tangential sealing can be as important as that of radial sealing. Since tangential and radial sealing are usually, but not always, attained through separate mechanisms, the scroll members of this invention may be employed in scroll-type apparatus using different tangential sealing techniques. However, since the unique tangential sealing means described in the above-identified copending applications Ser. Nos. 368,907 and 408,912, and referred to as radially compliant linking means, are believed to represent an important advance in scroll-type apparatus, the scroll member construction of this invention will be illustrated in a scroll compressor including the tangential sealing means disclosed in Ser. No. 408,912 now U.S. Pat. No. 2,924,977. In this copending application there is disclosed scroll apparatus which provides means to control the radial contacting forces such that tangential sealing is continuously and effectively attained even with wear or when noncompressibles are temporarily present. This means to control radial contacting comprises means to counterbalance at least a fraction of the centrifugal force acting upon the orbiting scroll member and radially compliant mechanical linking means between the orbiting scroll and its drive means.

In one embodiment, the radially compliant mechanical linking means is capable of providing a centripetal force to counterbalance a fraction of the centrifugal force thereby leaving a portion of the centrifugal force available for achieving controlled radial sealing. In such an embodiment the compliant mechanical linking means incorporates mechanical springs to counteract a portion of the centrifugal force. In another embodiment of the drive mechanism of the apparatus described in Ser. No. 408,912, means separate from the radially compliant mechanical linking means, e.g., counterweights, are provided to counterbalance all or nearly all of the centrifugal forces acting upon the orbiting scroll member and the radially compliant linking means, i.e., mechanical springs, are incorporated to provide the desired tangential sealing forces. The scroll members are angularly positioned by a coupling of the sliding friction type or rolling element type; the radially compliant linking means may be a slide-link or swing-link; either one or both of the scroll members may be cooled and the contacting surfaces may be lubricated if desired. This latter type of tangential sealing embodying a swing-link will be used as illustrative of tangential sealing means in the apparatus described herein.

The principles of the operation of scroll apparatus have been presented in previously issued patents as well as in copending application Ser. No. 368,907, now U.S. Pat. No. 3,884,599. It is therefore unnecessary to repeat a detailed description of the operation of such apparatus. It is only necessary to point out that a scroll-type apparatus operates by moving a sealed pocket of fluid taken from one region into another region which may be at a different pressure. If the fluid is compressed while being moved from a lower to higher pressure region, the apparatus serves as a compressor; if the fluid is expanded while being moved from a higher to lower pressure region it serves as an expander; and if the fluid volume remains essentially constant independent of pressure then the apparatus serves as a pump.

The sealed pocket of fluid is bounded by two parallel planes defined by the end plates, and by two cylindrical surfaces defined by the involute of a circle or other suitably-curved configuration. The scroll members have parallel axes since in only this way can the continuous sealing contact between the plane surface of the scroll members be maintained. A sealed pocket moves between these parallel planes as the two lines of contact between the cylindrical surfaces move. The lines of contact move because one cylindrical element, e.g., a scroll member, moves over the other. This is accomplished, for example, by maintaining one scroll fixed and orbiting the other scroll.

Throughout the following description the term "scroll member" will be used to designate the component which is comprised of both the end plate and the element which define the contacting surfaces making movable line contacts. The term "wrap" will be used to designate the element making movable line contacts. These wraps have a configuration, e.g., an involute of a circle (involute spiral), arc of a circle, etc., and they have both height and thickness.

Figure 2:
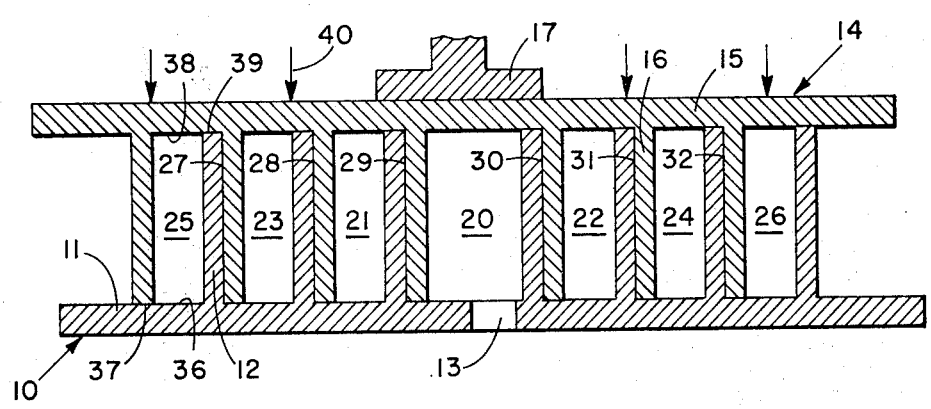
FIG. 2 is a cross section of the typical scroll-type apparatus of FIG. 1 through plane 2—2 of FIG. 1.

FIGS. 1 and 2 are presented to illustrate the general construction of scroll apparatus and the overall problems of radial and tangential sealing. The cross sectional views of FIGS. 1 and 2 show only end plates, wrap members and fluid pockets. A complete scroll-type apparatus embodying the scroll members of this invention is shown in FIGS. 26–29 and is described in detail below.

In FIGS. 1 and 2, the stationary scroll member 10 is seen to comprise an end plate 11 and a wrap 12. End plate 11 has a centrally located fluid port 13. For convenience in discussing the construction of the scroll members of this invention and the scroll-type apparatus in which these scroll members are incorporated, the scroll members will hereinafter be assumed to be used in a compressor. However, it will be apparent to those skilled in the art that the scroll members are equally applicable to scroll-type apparatus used as expansion engines or as pumps.

In FIGS. 1 and 2 the orbiting scroll member 14 is likewise formed of an end plate 15 and an involute wrap 16. In the simplified drawing of FIG. 2, the orbiting scroll member is shown to be attached to a drive shaft 17. In operation, the orbiting scroll member 14 is driven to describe an orbit while the two scroll members are maintained in a fixed angular relationship through the use of a suitable coupling means, not shown. In its orbiting motion, the orbiting scroll member defines one or more moving fluid pockets, i.e., pockets 20–26. These pockets are bounded radially by sliding or moving line contacts, i.e., contacts 27–32, lying generally on a line running through the center of the apparatus. As fluid is taken in from the peripheral zone 35 surrounding the wraps, it is introduced in the pockets and compressed as the pockets become smaller in volume as they approach the central pocket 20. Thus, provided efficient tangential sealing is effected along the moving contact lines defining the fluid pockets, and efficient radial sealing is achieved between the surface 36 of end plate 11 of stationary scroll member 10 and the end surface 37 of orbiting wrap 16 and between surface 38 of end plate 15 of orbiting scroll member 14 and the end surfaces 39 of stationary wrap 12, the pockets from outside inwardly will define zones of increasing fluid pressure and there will exist a pressure differential, $\Delta P$ across each line contact. It is therefore apparent that achieving radial contact between the wrap sides as they make sliding contact when the orbiting scroll member is orbited, seals against tangential leakage and hence attains tangential sealing. Likewise, the achieving of axial contact between the wrap ends and the end plate of the opposing scroll member seals against radial leakage and attains radial sealing. It will be appreciated that if the apparatus is an expansion engine, the zones of increasing fluid pressure will be in the same direction, i.e., from the center outwardly since compressed fluid is taken in through fluid port 13 and expanded fluid is discharged at the periphery.

As noted above, preferred apparatus for attaining the required tangential sealing while minimizing wear and linkage problems are described in copending U.S. Ser. Nos. 368,907; U.S. Pat. No. 3,884,599 and 408,912; U.S. Pat. No. 3,924,977. In addition, Ser. No. 408,912 describes an axial contacting or loading means in which high pressure fluid is introduced in a fluid chamber which is so positioned as to exert an axially directed pneumatic force on the scroll members to urge the wrap ends and end plates into axial contact. An alternate axial contacting or loading means, described in U.S. Ser. No. 561,478, uses a pressurizable fluid chamber within the scroll housing in axial force applying relationship with the orbiting scroll member. The compliance/sealing characteristic which is inherent in or added to the scroll member of this invention is, of course, designed to be used in conjunction with suitable means for developing axial and radial contacting forces of the type described in Ser. No. 408,912 or with any other suitable types of such means. It will be immediately apparent from the drawing of FIG. 2 that no matter what axial forces (illustrated by arrows 40) are brought to bear on the orbiting scroll member 14, when the scroll member is of a single rigid construction highly efficient radial sealing can not be attained unless wrap surfaces 37 and 39 and end plate surfaces 36 and 38 are very accurately machined. Moreover, the wraps must be formed to have the same heights throughout their entire lengths. Such machining can, of course, be attained at considerable expense; and it is also, of course, possible to construct each wrap to dimensions within the necessary tolerances, again at considerable expense. However, during operation, the advantages of the achievement of such accuracies can be materially depleted.

Figure 26:
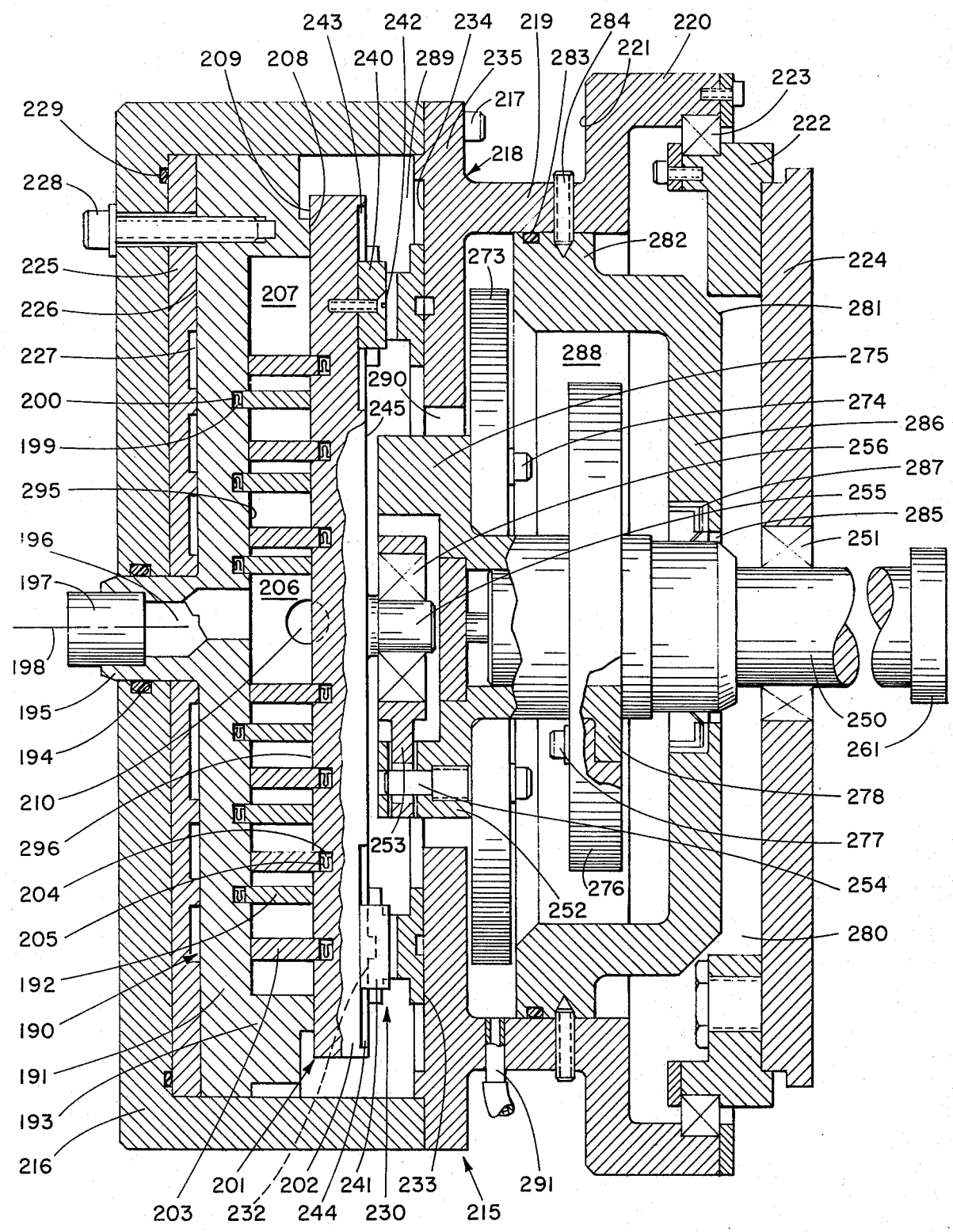
FIG. 26 is a longitudinal cross section of a scroll-type compressor constructed in accordance with this invention.

One factor involved in such a depletion is the radial temperature profile which will exist through the apparatus. In a compressor, the temperature of the fluid in the fluid pockets will increase radially inward and even though cooling means are provided (such as illustrated in FIG. 26) the wraps 12 and 17 will be subjected to a temperature differential causing the heights of the wraps to vary in accordance with the thermal expansion coefficient of the material from which they are formed. Another factor influencing the depletion of the advantages of the achievement of very accurate machining is the possibility of uneven wear within the apparatus during operation. It will be evident that if any unbalancing of the apparatus components occurs, it may cause uneven surface wear and lead, in turn, to unwanted leakage, even through these surfaces were accurately machined during manufacture.

By constructing the scroll member in accordance with this invention, i.e., by forming the wrap and end plates separately (in contrast to the one-piece construction shown in FIG. 2) it is possible not only to reduce the time and energy, and hence the cost, required for fabricating the scroll member but also at the same time to build into the scroll member axial compliance/sealing characteristics which are capable of maintaining the integrity of radial sealing no matter how it is achieved.

Figure 3:
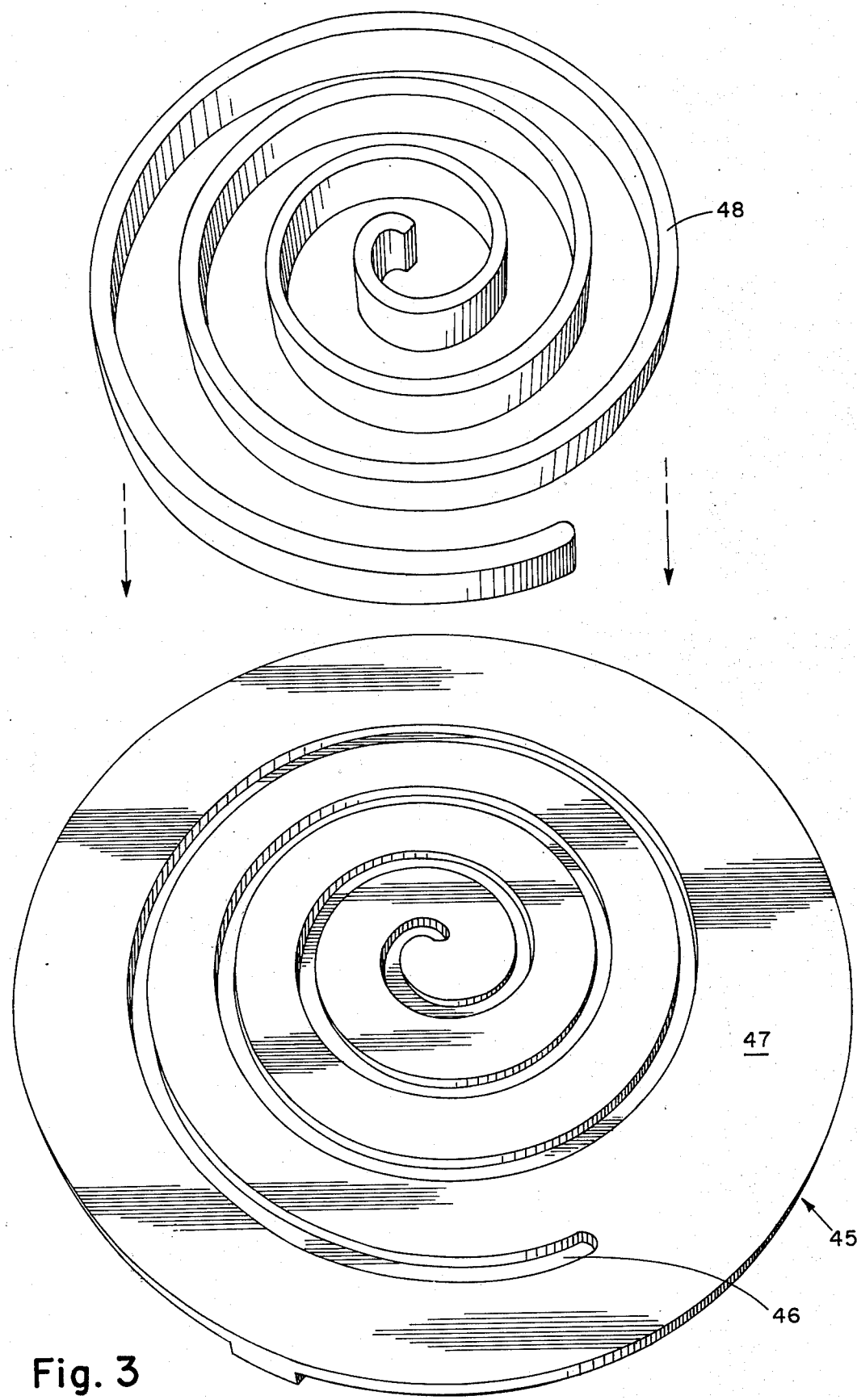
FIG. 3 is a perspective view of an end plate and an involute wrap, constructed according to this invention, prior to assembly.

FIG. 3 illustrates one embodiment of the construction of the scroll member of this invention and shows it just prior to assembly. The end plate 45 has a shallow involute groove 46 machined into its working face 47 using milling or electrical discharge machining, or other suitable forming techniques. An involute wrap member 48, configured to correspond to groove 46, is conveniently fabricated by casting techniques, molding techniques or by forming from strip material using, for example, roll forming apparatus. When wrap 48 is seated in groove 46, a scroll member is formed.

Although in most instances it will be desirable to form the separate end plate and wrap of a scroll member constructed in accordance with this invention of the same material, this is not necessary. In some cases it may be preferable to use different materials even to the extent that metallic and nonmetallic materials are used in the same scroll member.

The seating of the wrap in the groove may be such as to leave the wrap free to experience small axial and radial excursions within the groove; or it may be such as to rigidly affix the wrap to the end plate. In this first type of seating, it is preferable to include means within the groove to provide axial forces to impart to the wrap axial compliance/sealing characteristics which retain the integrity of the radial sealing. Such forces may be pneumatic, mechanical or a combination of both. In the second type of seating, used primarily for relatively large scroll members with thick wraps, it will be preferable to incorporate separate axial compliance/sealing means into the wraps.

Thus in one embodiment of the scroll member of this invention, the wrap "floats" within the involute groove to permit small axial and radial excursions of the wrap in the groove to give the scroll member inherent axial compliance/sealing characteristics. This can best be illustrated with reference to FIGS. 4 and 5 which show a fragmentary portion of a stationary and orbiting scroll member taken along a cross section through a moving line contact. Thus the cross section of FIGS. 4 and 5 are comparable to that portion of the apparatus of FIG. 2 where the wraps 12 and 16 make a moving line contact 31 to define fluid pockets 20 and 22.

Figure 4:
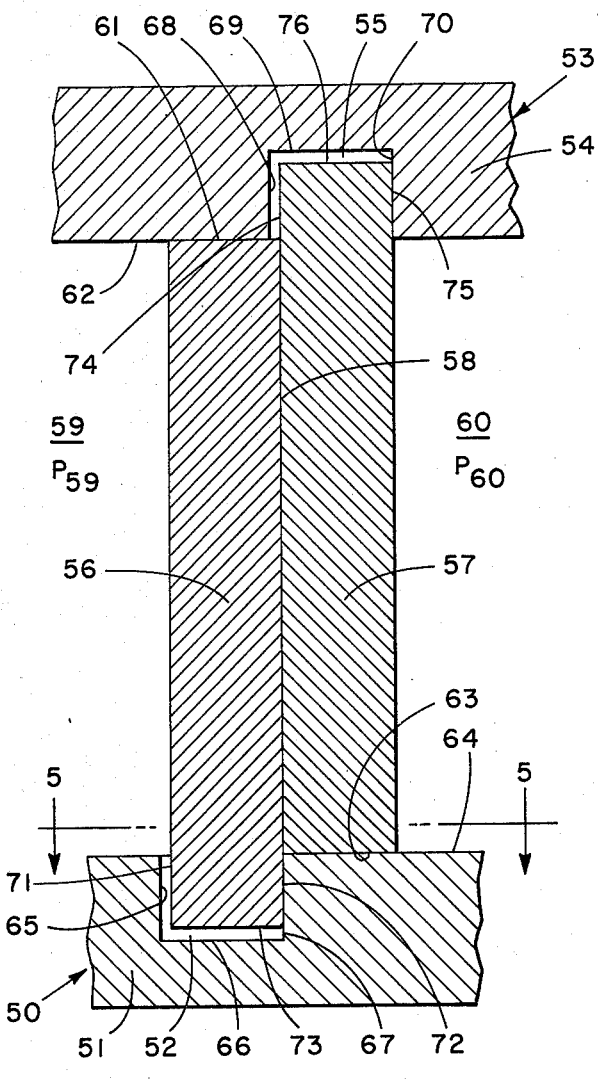
FIG. 4 is an enlarged fragmentary cross section of orbiting and stationary scroll members, constructed in accordance with this invention showing two involute wraps in line contact and the seating of the wraps in one embodiment of the groove which is cut into the end plate to attain axial compliance/ sealing through pneumatic forces.
Figure 5:
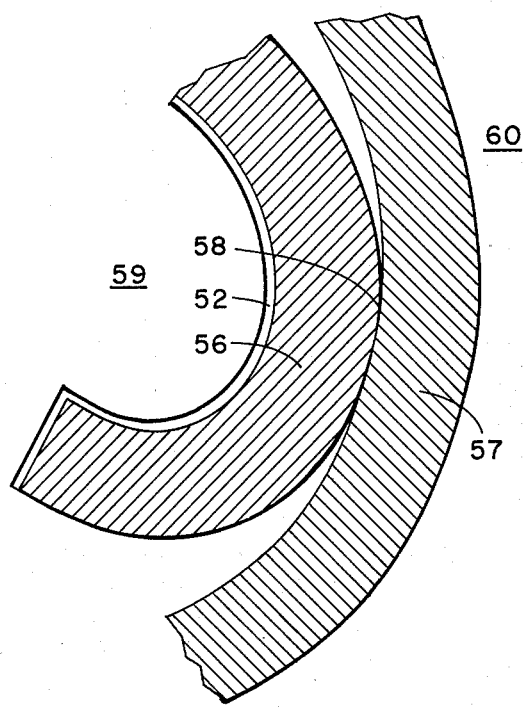
FIG. 5 is a cross section of the wraps of FIG. 4 taken through plane 5—5 of FIG. 4.

In FIG. 4, the stationary scroll member, designated generally by reference numeral 50 has an end plate 51 with an involute groove 52 similar to groove 46 of FIG. 3; and similarly the orbiting scroll member 53 has an end plate 54 with an involute groove 55. Involute wrap 56 is seated in groove 52 and is thus part of the stationary scroll member; while involute wrap 57 is seated in groove 55 and is thus part of the orbiting scroll member. These wraps, through the application of suitable radial forces, normally make a moving line contact 58 to effect the necessary tangential sealing.

In order to attain acceptable radial sealing, it is necessary for the end surface 61 of wrap 56 to make contact with surface 62 of end plate 54 and for the end surface 63 of wrap 57 to make contact with surface 64 of end plate 51. By permitting wraps 56 and 57 to float in their respective grooves, these conditions for radial sealing can be met, for a degree of axial compliance is imparted to the sealing. It is also necessary to maintain the integrity of the tangential sealing established within the apparatus, if it is to be an efficient compressor or expander. Thus the axial compliance inherent in the scroll members of this invention must be accompanied by the capability of maintaining the integrity of the tangential sealing.

FIG. 4 represents the simplest form of construction of the scroll member of this invention wherein pneumatic forces alone are used to impart axial compliance as well as to maintain tangential sealing. Groove 52 will be seen to have sides 65, 66 and 67 and groove 55 sides 68, 69 and 70; while that portion of wrap 56 which extends into groove 52 has contacting sides 71 and 72 and end 73; and wrap 57 has contacting sides 74 and 75 and end 76. Assuming that the scroll members of FIG. 4 are part of a compressor and that fluid pockets 59 and 60 are directly comparable to pockets 20 and 22 of FIG. 2, it will be apparent that fluid pressure $P_{59}$ obtaining in fluid pocket 59 is greater than the fluid pressure $P_{60}$ in adjacent fluid pocket 60. During scroll operation, a pressure differential $\Delta P = (P_{59} - P_{60})$ therefore exists across involute wraps 56 and 57 at the point 58 where they make sliding line contact, i.e., where tangential sealing is effected. As the compressor is started up and before $\Delta P$ has assumed any significant value, the wraps are free to float within their grooves. However as $\Delta P$ increases, the pressure of the fluid leaking into, say, groove 52 through the passageway defined between groove side 65 and wrap side 71 forces wrap 56 axially toward end plate 54 to make axial sealing contact through surfaces 61 and 62. Simultaneously, this fluid pressure forces wrap 56 radially outward to make contact between wrap side 72 and groove side 67 thus effectively sealing off pocket 59 from pocket 60. In like manner, high pressure fluid in groove 55 forces end surface 63 of wrap 57 to contact end plate surface 64 and wrap surface 75 to contact groove surface 70.

From FIG. 4, as well as those to follow, it will be seen that in seating the wrap in the end plate groove some form of an axial force applying means is provided to impart axial compliance/sealing characteristics to the wrap while minimizing fluid leakage through the channel in the groove defined between the wrap end walls and the sides of the groove. This minimizing of leakage thus maintains radial sealing throughout the scroll-type apparatus in which the scroll members of this invention are incorporated.

Although the embodiment of FIG. 4 is the simplest way of seating the wrap in the end plate groove, it does require very accurate geometry and finish for the contacting surfaces of the wrap and groove walls, i.e., surfaces 67/62 and 70/75. The contact pressures in both the axial and radial directions are dependent upon the fluid pressure that acts upon the two surfaces of the wrap and this fluid pressure is, as noted above, a function of $\Delta P$.

Figure 6:
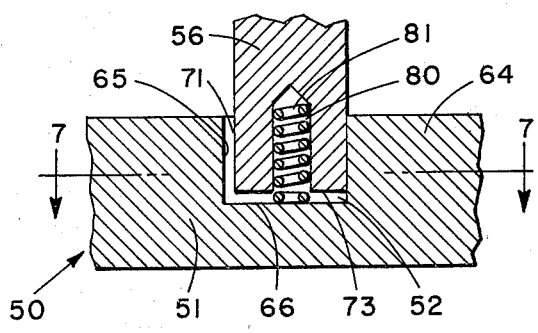
FIG. 6 is a fragmentary cross section of a scroll member illustrating the seating of the wrap in the groove of FIG. 4 to attain axial compliance/sealing through a combination of pneumatic and mechanical forces.
Figure 7:
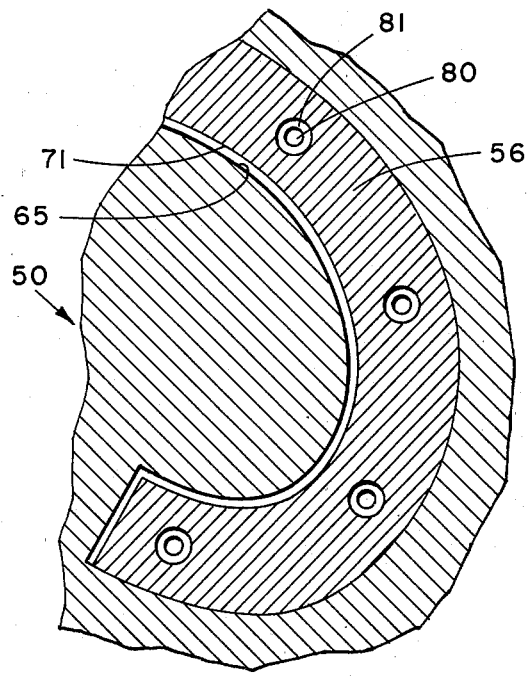
FIG. 7 is a cross section of the scroll member of FIG. 6 taken through plane 7—7 of FIG. 6.

In the scroll member shown in fragmentary detail in FIGS. 6 and 7, in which like reference numerals are used to identify like elements, a plurality of spaced springs in compression are used to provide the primary mechanical forces to urge the floating wrap 56 into engagement with the end plate of the opposing scroll; and pneumatic forces are used, as in the apparatus of FIG. 4, to maintain tangential sealing as well as to augment the axial force of the springs. To this end a number of periodically spaced spring wells 80 are drilled into the wrap end surface 73 and a spring 81 placed in each of them. The number and spacing of springs 81 must be such as to apply an essentially uniform spring force per circumferential unit length of the wrap.

Since springs 81 continuously apply a positive force on the wrap 56 to cause it to contact the surface of the opposing end member, essentially all of the required axial force is present even during start-up and shut-down, a fact which results in more reliable operation and during these periods than can be attained through the use of the apparatus of FIG. 4. However, as in the case of the apparatus of FIG. 4, the contacting surfaces of the wrap and groove sides must be capable of making precise fits.

Figure 8:
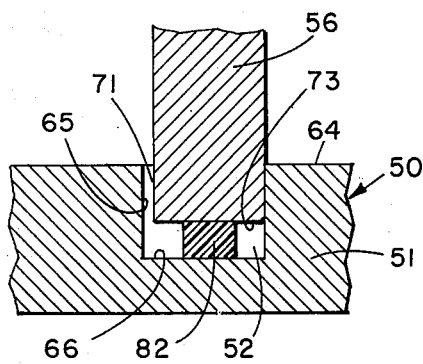
FIG. 8 is a fragmentary cross section of scroll member illustrating the seating of the wrap in the grooves of FIG. 4 to attain axial compliance/sealing through the use of an elastomeric element.

The embodiment of FIG. 8, like that of FIG. 6, uses mechanical means, i.e., an elastomeric member 82, to urge the wrap 56 into contact with the end plate surface of the opposing scroll member. This elastomeric member 82 may conveniently be formed of a hard rubber (natural or synthetic) or of other similar material. Although the pressure differential existing across the wrap members may be used, as in the apparatus of FIGS. 4 and 7, to provide fluid pressure to force wrap 56 radially outward to maintain radial sealing, this is not necessary. The elastomeric member 82 serves essentially the same purpose as springs 81. However, because there also exists a positive force in both axial directions, the elastomeric member is continuously caused to contact surface 73 of the wrap and surface 66 of the groove, thus providing an additional radial sealing means by preventing gas leakage under the wrap. The wrap sealing embodiment of FIG. 8 preferably finds use in apparatus wherein maintenance can be performed regularly, for the materials from which the elastomeric seal member are made may tend to deteriorate and so these seals may require replacement. Such elastomer members 82 can not, of course, be used in machinery in which the fluid being handled is corrosive to or reactive with the elastomeric material.

Figure 9:
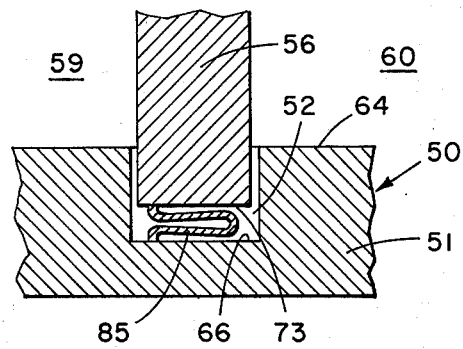
FIG. 9 is a fragmentary cross section of a scroll member illustrating the seating of the wrap in the groove of FIG. 4 to attain compliance/sealing through the use of a spring/seal.
Figure 10:
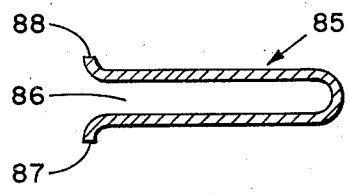
FIG. 10 is an enlarged cross section of the one embodiment of the spring/seal used in the embodiment of FIG. 9.
Figure 11:
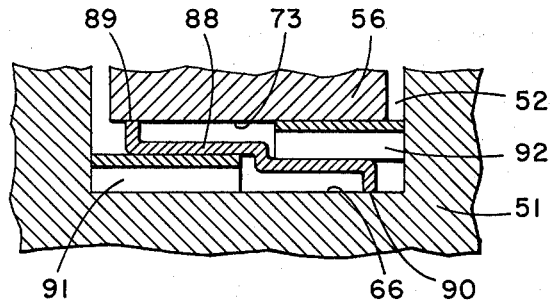
FIG. 11 is an enlarged cross section of another embodiment of a spring/seal useable to seal the wraps in the grooves.
Figure 12:
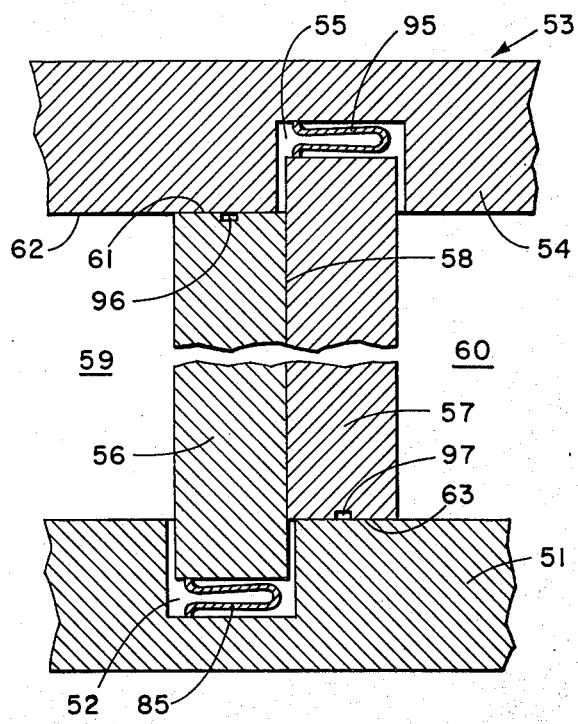
FIG. 12 is a fragmentary cross section of orbiting and stationary scroll members using the spring/seal of FIG. 10 and having lubricant channels.

FIGS. 9–12 illustrates the use of a spring/seal as a mechanical means for forcing wrap 56 to make contact with the end plate to achieve radial sealing while simultaneously providing a gas-tight seal in the seating of wrap 56 to maintain the integrity of the tangential sealing within the apparatus. In FIGS. 9, 10 and 12 this spring/seal is a U-shaped spring 85. U-shaped spring 85, configured to conform with the involute shape of the groove and wrap, is formed so that when it is installed as shown in FIG. 9 it is in compression. It is placed so that its open end 86 is facing toward the pocket containing the fluid at the higher pressure. In its compressed state in groove 52, end 87 (FIG. 10) makes a sealing contact with surface 66 of groove 52; and end 88 makes sealing contact with end surface 73 of wrap 56. Thus no gas can leak from pocket 59 into pocket 60 through groove 52.

Another embodiment of a spring/seal is illustrated in FIG. 11. This spring/seal comprises an involutely configured stepped seal strip 88, the surfaces of the two ends 89 and 90 of which make sealing contact with surfaces 73 and 66, and two opposing involutely configured wave springs 91 and 92 which urge ends 89 and 90 against these surfaces. Thus, the spring/seal may be formed as a single member as is U-shaped spring 85, or as a plurality of interacting members as shown in FIG. 11.

Because spring/seals of the type illustrated in FIGS. 10 and 11 eliminate gas leakage, all of the surfaces involved on the wraps and grooves may be machined to conventional tolerances while at the same time making it possible to obtain superior results. These superior results come about by reason of the fact that radial sealing is attained through a shifting contact between the wrap and the opposing scroll end plate which is determined by the compression force of the spring/seal and relatively independent of $\Delta P$. The embodiment of FIGS. 9–12 therefore represents a balanced pressure seal element which is inherent in the construction of the scroll member and a preferred means for seating the wraps in the grooves.

FIG. 12 illustrates the application of the scroll member construction of this invention using the U-shaped spring 85 to both the orbiting and stationary scroll members and it further illustrates the incorporation of oil grooves. It will be seen that identical arrangements are used. Thus wrap 57 is seated in groove 55 through U-shaped spring 95 in the same manner that wrap 56 is seated in groove 54 through U-shaped spring 85.

FIG. 12 also illustrates the use of oil grooves 96 in wrap 56 and 97 in wrap 57. Oil delivered to these grooves (by means as shown for example in FIG. 26) provides lubrication for contacting wrap end 61 and end plate surface 62 and for contacting wrap end 63 and end plate surface 64. It is, of course, within the scope of this invention to include such oil grooves in the contacting wrap ends of the scroll members illustrated in FIGS. 4–8.

Figure 13:
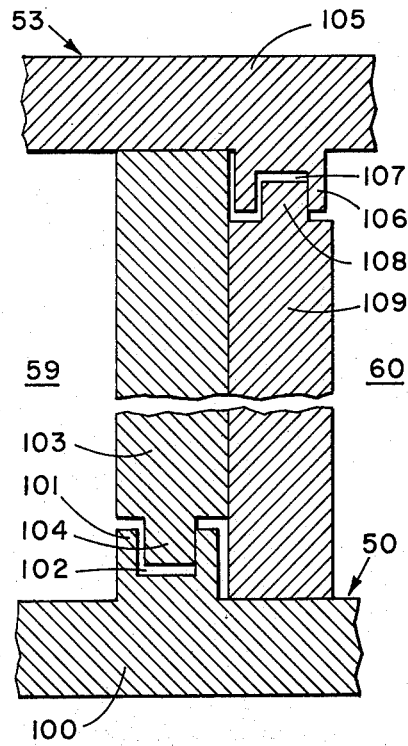
FIG. 13 is a fragmentary cross section of a scroll member, constructed in accordance with this invention, showing the seating of the wrap in another embodiment of the groove, which is defined within a track machined on the end plate surface, to attain axial compliance/sealing through pneumatic forces.

FIG. 13 illustrates another embodiment of the scroll member of this invention wherein the involute groove in the end plate is formed as a raised track on the end plate surface. The wrap has a centrally-positioned extension to fit into the groove defined within this track. As shown in FIG. 13 the stationary scroll member 50 has an end plate 100 with an involutely configured track 101 having a central groove 102 throughout its length. This track 101 has a width slightly less than the width or thickness of stationary wrap 103. Wrap 103 terminates at the end through which it is joined to end plate 100 or seated in groove 102 in a central involute extension 104, the width of which is slightly less than the width of groove 102. In like manner orbiting scroll member 53 has an end plate 105 with an involutely configured track 106 in which there is a central groove 107 adapted to seat central extension 108 of orbiting scroll wrap 109.

Figure 14:
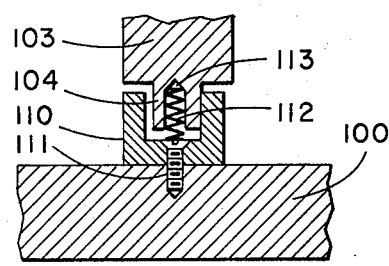
FIG. 14 is a fragmentary cross section of a scroll member illustrating the seating of the wrap in the groove of FIG. 13 to attain axial compliance/sealing through a combination of pneumatic and mechanical forces.
Figure 15:
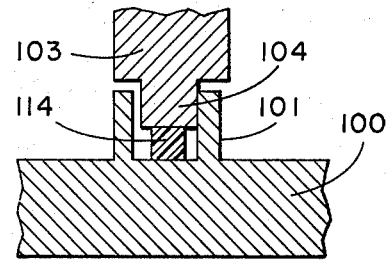
FIG. 15 is a fragmentary cross section of a scroll member illustrating the seating of the wrap in the groove of FIG. 13 to attain axial compliance/sealing through the use of an elastomeric element.
Figure 16:
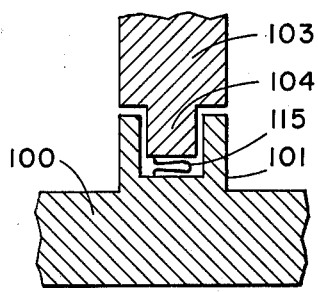
FIG. 16 is a fragmentary cross section of a scroll member illustrating the seating of the wrap in the groove of FIG. 13 to attain compliance/sealing through the use of a U-shaped spring/seal.

In operation, the scroll members of FIG. 13 function in the same manner as described above for the scroll members illustrated in FIG. 4. That is, both axial and radial forces bearing on the wraps 103 and 109 are pneumatic and a function of ΔP. In a similar manner the scroll members illustrated in fragmentary cross sections in FIGS. 14, 15 and 16, using the wrap and groove configurations of FIG. 13, are assembled through the same means as those in FIGS. 6, 8 and 9, respectively. That is, in FIG. 14 a plurality of spaced springs 112 in spring wells 113 in wrap extension 104 provide the primary axial force while fluid pressure is used to maintain the integrity of the tangential sealing means; in FIG. 15, an elastomer member 114 provides axial forces and a tangential seal; and in FIG. 16 the U-shaped spring 115 provides a balanced seal. FIG. 14 also illustrates the fact that track 110 may be a separate member affixed through screws 111 to the end plate instead of being integral with it as in FIG. 13.

It is also within the scope of the invention to rigidly mount the separate wrap in the end plate groove to form the scroll member. A scroll member in which the wrap is rigidly mounted in the end plate does not possess any inherent axial compliance/sealing characteristic as is possessed by those in which the wrap is permitted small axial and radial excursions in its groove as shown in the preceding FIGS. 4–16. It is, therefore, usually preferable to rigidly mount those wraps which possess sufficient thickness to permit them to have separate axial compliance/sealing means associated with them. Such axial compliance/sealing means for conventionally constructed scroll members are discribed in detail in copending application Ser. No. 561,479. Several embodiments of these separate axial compliance/sealing means are illustrated in FIGS. 17–25.

As noted above in the discussion on radial sealing and the desirability of being able to use conventional tolerances in machining wrap ends and end plate surfaces, the problem involves providing a degree of compliance in the axial contacting of the surfaces which give rise to radial sealing while at the same time maintaining the integrity of the tangential sealing within the apparatus. As will be seen in the various embodiments of axial compliance/sealing means illustrated, a separate seal element is used with each wrap and pneumatic forces, mechanical forces or a combination of these types of forces may be used to actuate the seal element to urge it into contact with the opposing end plate surface. These forces will be recognized to have their direction counterparts in the axial and radial forces applied to the separate floating wraps.

Figure 17:
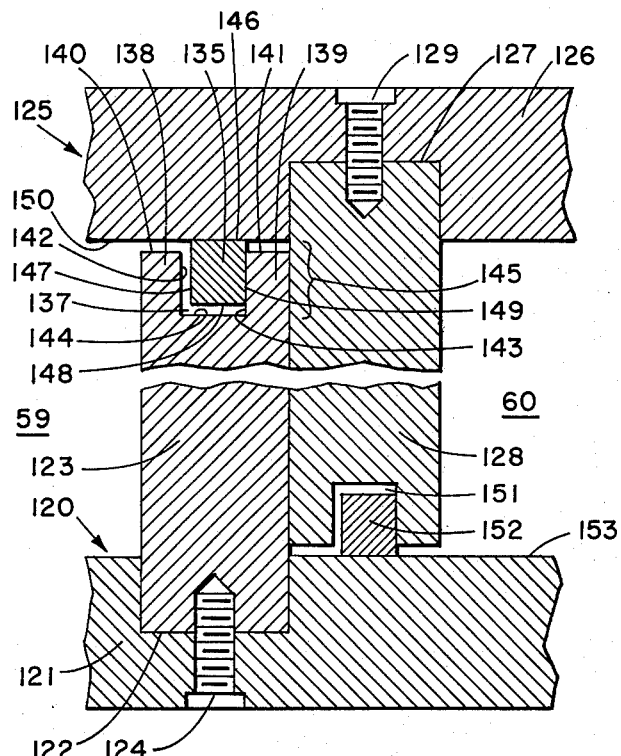
FIG. 17 is a fragmentary cross section of orbiting and stationary scroll members showing the rigid attachment of the wraps to the end plates and the incorporation of one embodiment of separate axial compliance/sealing means using pneumatic forces to actuate them.

FIG. 17 illustrates in fragmentary cross section a stationary scroll member 120 having an end plate 121 with an involute groove 122 in which a stationary wrap 123 is rigidly mounted such as through the use of a plurality of spaced screws 124. In like manner the orbiting scroll member 125 has an end plate 126 with an involute groove 127 having an involute wrap 128 rigidly mounted therein through a plurality of spaced screws 129. The separate axial compliance/sealing means used with the rigidly attached separate wraps may be generally defined as comprising a seal element configured to conform to the shape of the wrap and means to actuate the seal element by urging it into contact, with a preselected preload, with the opposing scroll member end plate. These means to urge the spring/seal element into contact with the opposing scroll member end plate are positioned within a fluid volume defined within either the wrap end or within the seal element, depending upon the embodiment of seal element used. The compliance/sealing means are, of course, associated with the involute wraps of both orbiting and stationary scroll members. as shown in FIG. 17. In FIGS. 18–20 and FIGS. 22–25 these compliance/sealing means are shown only for the stationary scroll member.

In the embodiment of the seal element of FIGS. 17–21, this component takes the form of a sealing member, generally but not necessarily of a rectangular cross section, which has an involute configuration corresponding to the configuration of the involute wrap member, e.g., stationary wrap 123 in the drawings, with which it is used. This involute seal member may be formed of a metallic or nonmetallic material. exemplary of metallic materials are cast iron, steel, bronze and the like and of nonmetallic materials are carbons or plastics such as polytetrafluoroethylene (filled or unfilled), polyimides, and the like. Such material may be of a character as to require lubrication or it may be capable of running dry, in which latter case it is preferably a self-lubricating material such as a filled polytetrafluoroethylene.

In FIG. 17 the seal element 135 is shown to be rectangular in cross section and the contacting surface of stationary wrap 123 is grooved to define a channel 137, the width of which is slightly greater than the width of seal element 135. The groove defining involutely-configured channel 137 is, as will be seen in FIG. 17, formed of two parallel involute extensions 138 and 139, having end surfaces 140 and 141 and side walls 142 and 143, respectively. Surface 144 completes the walls of the grooves.

Together spring seal element 135 and channel 137 define the boundaries of the compliance/sealing means 145. Seal element 135 can be seen to have four sides 146, 147, 148 and 149. This basic structure of seal element and groove configuration is maintained throughout the spring seal embodiment illustrated in FIGS. 17-21.

FIG. 17, as does its counterpart wrap seating arrangement of FIG. 4, represents one of the simplest structures of a compliance/sealing means. In this embodiment, pneumatic forces alone are used to urge sealing surface 146 of seal element 135 in contact with surface 150 of end plate 126 of the orbiting scroll member and seal element surface 149 in contact with groove wall 143 to maintain tangential sealing. Assuming that the apparatus (illustrated in fragmentary detail in FIG. 17) is a compressor, as in FIG. 4, then radial sealing is attained through a pneumatic force proportional to $\Delta P = (P_{59} - P_{60})$ as in the case of the floating wrap 56 of FIG. 4. Tangential sealing is also maintained through pneumatic forces in the same manner as described in conjunction with FIG. 4.

In a similar construction, wrap 128 of orbiting scroll member 125 has a groove 151 in which is positioned a seal element 152 for making sealing contact with surface 153 of the end plate 121 of stationary scroll member 120.

Although the embodiment of FIG. 17 is the most simple configuration of an axial compliance/sealing means, it does require very accurate geometry and finish for the contacting surfaces of the seal element and groove walls, i.e., surfaces 143 and 149. The contact pressures in both the axial and radial directions are dependent upon the fluid pressure that acts upon the two surfaces of the spring seal element and this fluid pressure is, as noted above, a function of $\Delta P$. The choice of material from which to construct the seal element in the compliance/sealing means shown in FIG. 17 is dependent upon such factors as the kind of operating environment, the operational life desired, operating temperature, type of lubrication used and convenience and cost of manufacturing techniques used.

Figure 18:
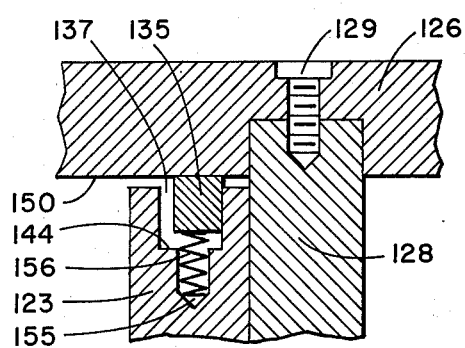
FIG. 18 is a fragmentary cross section of contacting wraps attached to the end plates as in FIG. 17 and having separate axial compliance/sealing means using a combination of pneumatic and mechanical forces to actuate them.

In the compliance/sealing means used in the scroll members shown in fragmentary detail in FIG. 18 a plurality of spaced springs in compression are used as the primary means to urge the seal element into engagement with the end plate of the opposing scroll; and pneumatic means are used, as in the apparatus of FIG. 17, to maintain tangential sealing as well as to augment the axial force of the springs. To this end a number of periodically spaced spring wells 155 are drilled into groove surface 144 and a spring 156 placed in each of them. The number and spacing of springs 156 must be such as to apply an essentially uniform spring force per circumferential unit length of the seal element.

Since springs 156 continuously apply a positive force on the seal element 135 to cause it to contact the surface of the opposing end member, essentially all of the required axial force is present even during start-up and shut-down. However, as in the case of the apparatus of FIG. 17, the contacting surfaces of the seal element and the surfaces of the channel must be capable of making precise fits. The choice of material for the seal elements of FIG. 18 depends upon essentially the same factors as those listed above for the FIG. 17 embodiment.

Figure 19:
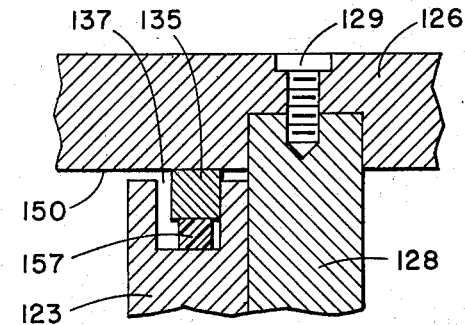
FIG. 19 is a fragmentary cross section of contacting wraps attached to the end plates as in FIG. 17 and having separate axial compliance/sealing means using an elastomeric element to actuate them.

The embodiment of FIG. 19, like that of FIG. 18, uses mechanical means, i.e., an elastomeric member 157 to urge the seal element 135 into contact with the end plate surface 150 of the opposing scroll member. This elastomeric member 157 may conveniently be formed of a hard rubber (natural or synthetic) or of other similar material. The elastomeric member 157 serves essentially the same purpose as springs 156. However, because there also exists a positive force in both axial directions, the elastomeric ring is continuously caused to contact the surfaces of the seal element and of the groove, thus maintaining the integrity of the tangential sealing in the apparatus. As in the case of the scroll member of FIG. 8, the scroll members of FIG. 19 find use in apparatus wherein maintenance can be performed regularly because of the properties of the materials from which the elastomeric member is made.

Figure 20:
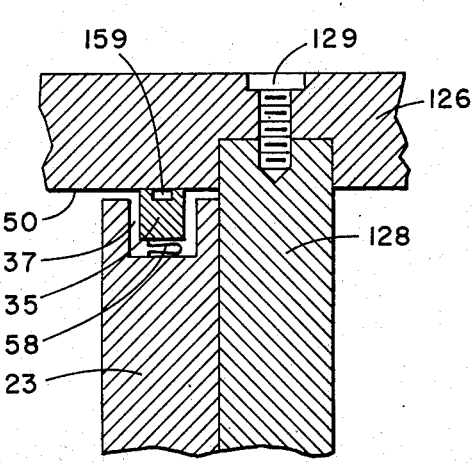
FIG. 20 is a fragmentary cross section of contacting wraps attached to the end plates as in FIG. 17 and having separate axial compliance/sealing means using a U-shaped spring/seal to actuate them.

FIG. 20 illustrates the use of a U-shaped spring/seal 158 as a mechanical means for forcing the seal element 135 to make contact with the end plate to achieve radial sealing. This U-shaped spring/seal 158 which is identical to that of FIG. 10, also provides a gas-tight seal under seal element 135 to maintain the integrity of the tangential sealing within the apparatus. As in the case of its use in seating a wrap (e.g., in FIG. 12) the U-shaped spring/seal 158 eliminates gas leakage; and hence all of the surfaces involved in the compliance/sealing means may be machined to conventional tolerances while at the same time making it possible to obtain improved results. It is also, of course, within the scope of this invention to use other embodiments of a spring/seal such as that shown in FIG. 11. Finally, FIG. 20 illustrates the incorporation of an oil groove 159 in the seal element. Similar oil grooves may, of course, be incorporated into any of the compliance/sealing means shown in FIGS. 17-20.

As pointed out previously, in construction the scroll member of this invention the wrap may be seated in the end plate to impart compliance/sealing characteristics to the structure and therefore additional compliance/sealing means are not required. However, in some special circumstances, it may be desirable to add compliance/sealing means to a scroll member in which the wrap is seated in the end plate groove in a manner to give the scroll member a degree of inherent compliance/sealing characteristiccs. Thus FIG. 21 illustrates such an arrangement.

Figure 21:
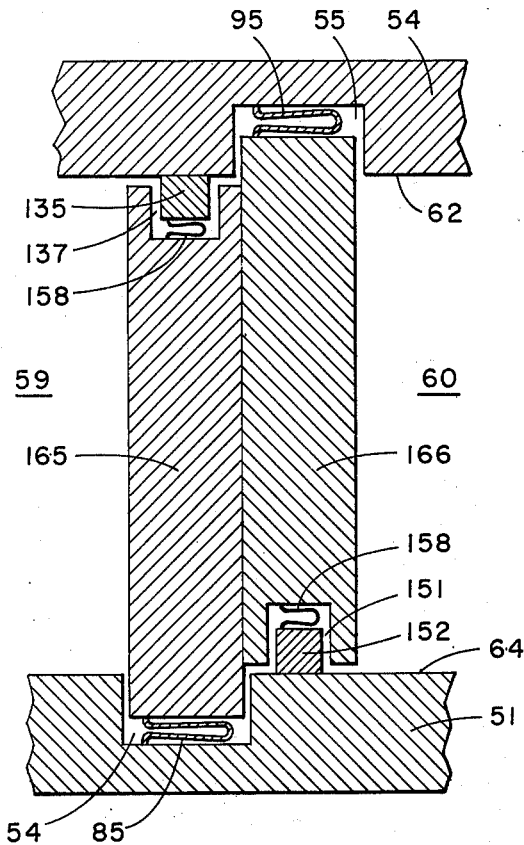
FIG. 21 is a fragmentary cross section of orbiting and stationary scroll members using a U-shaped spring/seal to seat the wraps in the end plates and additional axial compliance/sealing means also incorporating a U-shaped spring/seal.

In FIG. 21 the seating of the wrap 165 in end plate 51 and of wrap 166 in end plate 54 is accomplished in the manner shown in FIG. 12 and an auxiliary compliance/sealing means such as that of FIG. 20 is added. This arrangement minimizes the amount of machining required for all those surfaces involved in the axial sealing of the apparatus and contributes an added degree of axial compliance.

FIGS. 22-25, in which like elements are given the same reference numbers in FIGS. 16-20, illustrate another embodiment of the seal element. As will be seen in FIG. 22, seal element 170 is configured as a trough to define a chamber 171, and the end of wrap 123 has a central extension member 172 extensible into chamber 171. Seal element 170 has an radial sealing surface 173 for making contact with surface 150 of the orbiting scroll member end plate 126; and side pieces 174 and 175 of sealing element 170 have internal surfaces 176 and 177, respectively. Central extension member 172 of the wrap has surfaces 178 and 179 for contacting surfaces 176 and 177 to maintain tangential sealing. Thus in the apparatus illustrated in FIG. 22, surfaces 176 and 178 will be in contact for this purpose whether the device is a compressor or an expander. The width of chamber 171 within the spring seal element must be slightly greater than the width of wrap extension 172 to define a fluid passage around the extension and within chamber 171. It is also necessary that the overall width of spring seal element 170 be slightly less than the width of the wrap with which it is associated. This is required to provide the seal element some radial motion.

Figure 22:
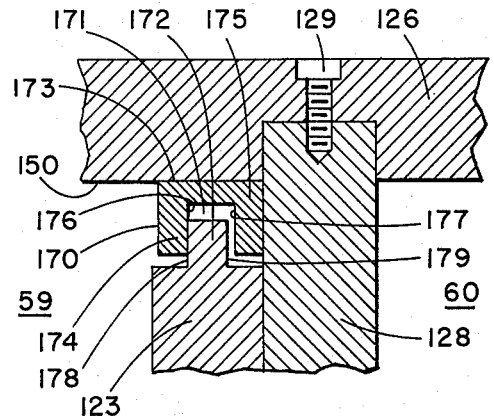
FIG. 22 is a fragmentary cross section of rigidly attached wraps and the incorporation of another embodiment of separate axial compliance/sealing means using pneumatic forces to actuate them.

It will be seen that the compliance/sealing means of FIG. 22 functions in the same manner as that described for the compliance/sealing means of FIG. 17. Fluid pressure derived from pocket 59 provides a pneumatic force to urge seal element 170 into contact with end plate surface 150 as well as to force contact between surfaces 176 and 178 to maintain tangential sealing. As in the case of the embodiment of FIG. 17, the embodiment of FIG. 22 is simple in configuration, but it require surfaces 176/178 to be accurately machined.

Figure 23:
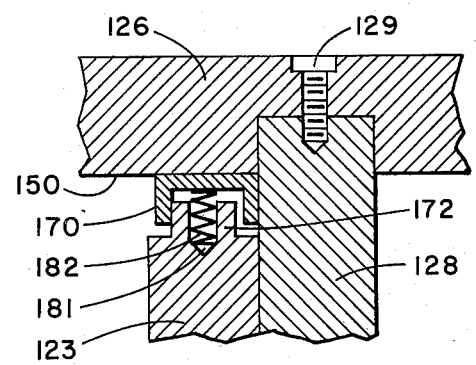
FIG. 23 is a fragmentary cross section of rigidly attached wraps and the incorporation of the FIG. 22 embodiment of separate coaxial compliance/sealing means using a combination of pneumatic and mechanical forces to actuate them.
Figure 24:
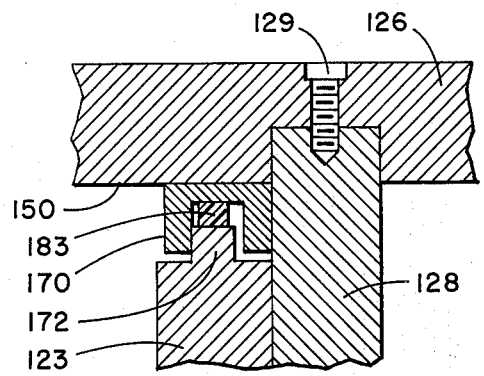
FIG. 24 is a fragmentary cross section of rigidly attached wraps and the incorporation of the FIG. 22 embodiment of separate axial compliance/sealing means using an elastomeric element to actuate them.
Figure 25:
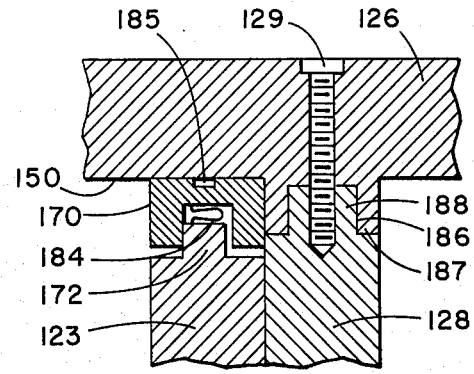
FIG. 25 is a fragmentary cross section of rigidly attached wraps and the incorporation of the FIG. 22 embodiment of separate axial compliance/sealing means using a U-shaped spring/seal to actuate them.

In the embodiment of FIG. 23, the wrap extension 172 has a plurality of spring wells 181 drilled in it and they contain springs 182 in compression to urge spring seal element 170 in the axial direction to contact surface 150. Essentially the same design considerations and performance characteristics pertain to the embodiment of FIG. 23 as were described above for the embodiment of FIG. 18. Likewise, the embodiments of FIGS. 24 and 25 are directly comparable in operation to those of FIGS. 19 and 20. FIG. 24 illustrates the use of an elastomeric sealing member 183 with the compliance/sealing means of FIG. 22. FIG. 25 illustrates the use of a spring/seal 184 e.g., that shown of FIG. 10, in these compliance/sealing means. The spring/seal of FIG. 11 is, of course, equally acceptable. FIG. 25 shows a lubricant channel 185 in the seal element 170, an arrangement which is, of course, also applicable to the embodiments of FIGS. 22–24. Finally, FIG. 25 also illustrates the fact that the scroll member construction of FIG. 13, in which a groove 186 is defined on the end plate surface within a track 187 and the wrap 128 has a central extension 188, is applicable to that scroll member embodiment of this invention in which the wrap is rigidly mounted in the groove in the end plate.

Figure 27:
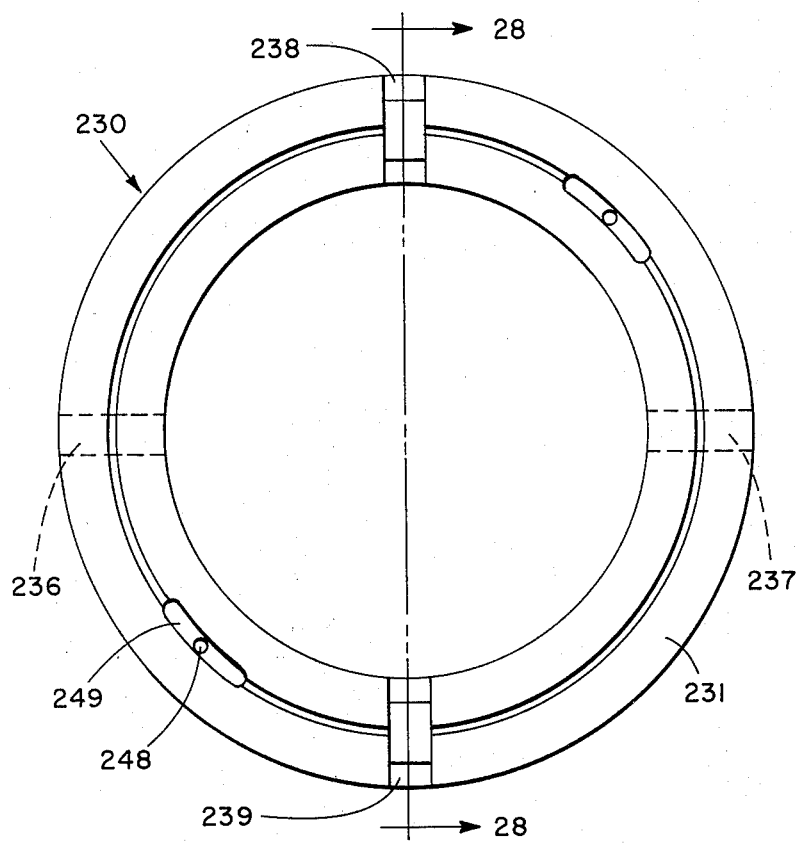
FIG. 27 is a top plan view of the coupling means of the compressor of FIG. 26.
Figure 28:
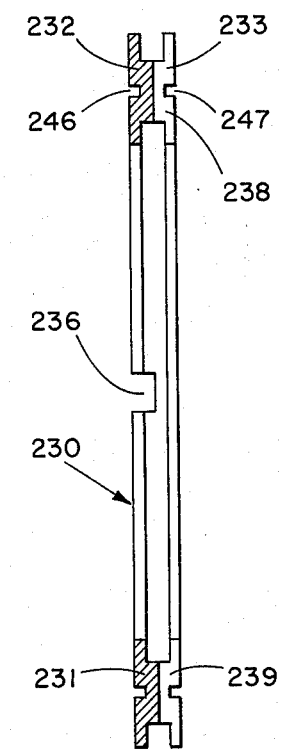
FIG. 28 is a cross section of the coupling means of FIG. 27 taken through plane 28—28 of that figure.
Figure 29:
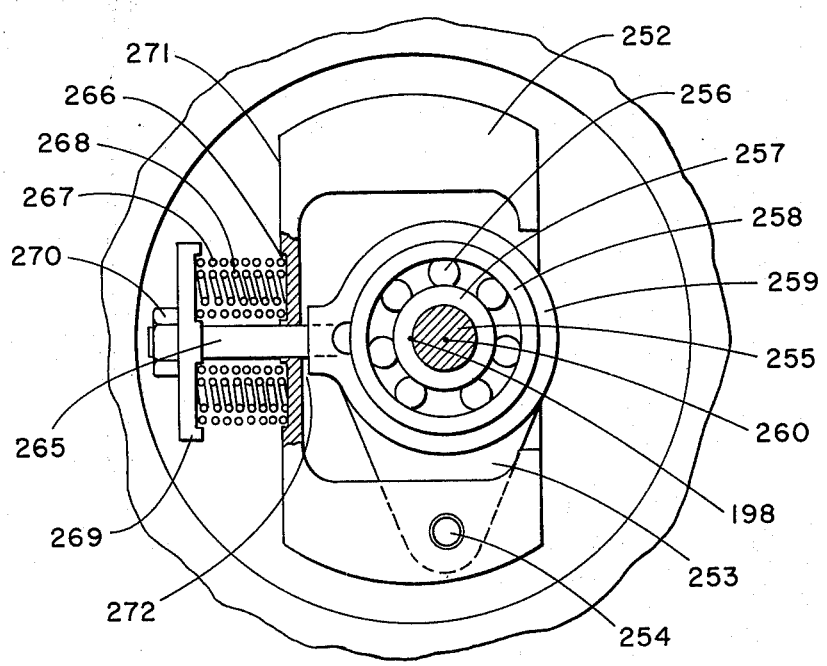
FIG. 29 is a top plan view of the orbiting scroll member driving means of the compressor of FIG. 26.

A compressor constructed in accordance with this invention is shown in longitudinal cross section in FIG. 26. Reference should also be had to FIGS. 27–29 where indicated. In all of these drawings like reference numerals are used to refer to like elements. As seen in FIG. 26 the stationary scroll member, generally indicated at 190, is comprised of an end plate 191 terminating in an enlarged peripheral ring 193; a wrap 192 similar to that shown in FIG. 3; an annular sealing ring member 194; and a central ported extension 195. Within extension 195 is a high-pressure fluid passage 196 and extending into it is a connector tube 197, aligned on the machine axis 198, for connecting a high-pressure line, not shown. In accordance with this invention, end plate 191 of stationary scroll member 190 is formed to have an involute groove 199 in which wrap 192 is seated according to any one of the wrap seating means embodiments illustrated in FIGS. 4–16. In FIG. 26 this is illustrated in a somewhat simplified way by showing an involutely configured U-shaped spring/seal 200 in groove 199 as exemplary of an axial force applying means in the embodiment of the scroll member of this invention wherein axial compliance/sealing is inherent in the scroll member construction. It is also, of course, within the scope of this invention to construct the scroll members with separate wraps rigidly mounted in the end plate and to incorporate in the apparatus, if desired, axial compliance/sealing means such as illustrated in FIGS. 17–25.

The orbiting scroll member, generally indicated at 201, comprises an end plate 202 and a wrap 203, also structured as shown in FIG. 3. Wrap 203 is set in an involute groove 204 in end plate 202 and is seated through an involute U-shaped spring 205 in the same manner as in the stationary scroll member. The fluid pockets, e.g., central pocket 206 at highest fluid pressure and peripheral pocket 207, along with all of the other pockets in between at intermediate pressures increasing radially inward, are isolated from the remaining volume defined within the compressor. To this end, peripheral ring 193 of stationary scroll member 190 has a surface 208 which makes sealing contact with inner surface 209 of end plate 202 of orbiting scroll member 201. The need for this isolation will be discussed below. The zone of highest pressure, i.e., fluid pocket 206, communicates with a high-pressure line or source (not shown) through fluid passage 196 and connector tube 197. The low-pressure peripheral chamber 207 communicates through one or more low-pressure ports 210 with a low-pressure fluid source or reservoir (not shown). If the apparatus is a compressor, low-pressure fluid is brought in through low-pressure port 210 and compressed fluid is delivered through a suitable conduit connected to connector tube 197. If, on the other hand, the apparatus is used as an expander, high-pressure fluid is brought in through passagae 196 and expanded low-pressure fluid is discharged through one or more low-pressure ports 210.

The scroll apparatus is contained within a housing, generally indicated at 215, which in the embodiment of FIG. 26 comprises a front housing cover plate 216 affixed through screws 217 to housing back plate 218 having a smaller diameter section 219 and a larger diameter section 220 joined through a shoulder 221. Within larger diameter section 220 is an annular ring 222 mounted thereto through bearing 223; and affixed to annular ring 222 is a back cover 224.

Interposed between end plate 191 of stationary scroll member 190 and the inner end wall of front housing cover plate 216 is a plate 225 having an involute groove which defines with the front side 226 of end plate 191 an involute channel 227 suitable for circulating a cooling fluid. End plate 191 and plate 225 are rigidly held within housing by a plurality of cap screws 228 and plate 225 is peripherally sealed to front plate housing through an o-ring seal 229.

The orbiting scroll member must be prevented from moving angularly with respect to the stationary scroll member and with respect to the frame of the housing; and in this embodiment it must be driven through radially compliant means in an orbit in a way to counteract all or a portion of the centrifugal force developed in its orbiting while providing the required radial forces to achieve tangential sealing.

The maintaining of the desired angular relationship between the orbiting scroll and the fixed scroll member and housing is accomplished through the use of a coupling member generally indicated by the numeral 230. As will be seen in FIGS. 27 and 28, this coupling member comprises an annular ring 231 with an H-shaped cross section. What may, for convenience, be designated the front surface 232 faces the orbiting scroll; and in keeping with this terminology, the opposite surface, called the back surface 233, faces the inside wall 234 of an internal supporting frame member 235 of the housing. Front surface 232 has two oppositely disposed keyways 236 and 237 cut into it (FIG. 27); and back surface 233 also has two oppositely disposed keyways 238 and 239 cut into it. The axes of the keyways on the front and back surfaces are at right angles. The keys which slidingly engage these keyways are attached to the orbiting scroll and the housing frame member 235. As will be seen in FIG. 26, keys 240 and 241 are fastened, such as by countersunk screws 242, into shallow recesses 243 and 244 cut into external surface 245 of the orbiting scroll member end plate. These keys slide in keyways 236 and 237 of the coupling member, respectively. In like manner internal surface 234 of housing frame member 235 has two oppositely disposed keys (not shown) mounted thereon for making sliding engagement with keyways 238 and 239 of the coupling.

Inasmuch as there is sliding friction contact between the front and back surfaces of the coupling and the surfaces of the orbiting scroll member end plate and the support frame, it may be desirable to lubricate these surfaces. This may be done by introducing lubricating oil into the apparatus in accordance with known practice. To this end coupling 230 may have lubricant channels 246 and 247 cut on its front and back surfaces and joined through passageways 248 extending between arcuate channel 249 (FIGS. 27 and 28).

Several embodiments of suitable mechanisms for driving the orbiting scroll member with the desired radial compliance to attain a predetermined tangential sealing force and described in Ser. No. 408,912. The embodiment chosen for illustrating a suitable mechanism in FIG. 26 is one in which a swing-link is used and means are provided to counterbalance a portion of the centrifugal forces acting upon the stationary scroll member. The importance of radial forces to prevent tangential leakage has already been disccussed. Tangential sealing should therefore be accomplished in a manner to introduce a degree of radial compliance, as well as axial compliance, into the system. It is also, of course, preferable to attain this radial compliance without the expenditure of excessive time and energy normally required is machining to achieve highly accurate machine tolerances.

In order to attain this radial compliance, the orbiting scroll member must have the ability to move inwardly or outwardly relative to the machine axis in response to gradual wear of the scroll wraps or to encounter noncompressible objects such as a slug of liquid, accumulated wear debris or ingested dirt particles. This radial compliance feature also allows the use of less perfect geometry scrolls in that it allows the orbiting scroll member to ride inside of the fixed scroll member and adjust its trajectory, as required, to suit the geometries of the wraps of the two scrolls. In the embodiment of FIGS. 26 and 29 chosen to be representative of one way of attaining such radial compliance, a ball bearing is mounted on the axial drive shaft of the orbiting scroll member and the outer periphery of this ball bearing is connected to a crank mechanism with a swing-link. The axis of the swing-link is nominally perpendicular to the eccentricity radius of the orbiting scroll member. During rotation of the drive crank, the orbiting scroll member swings radially outward under the action of centrifugal force acting on its center of mass. The orbiting scroll member is confined to a given locus of motion by virtue of contact with the wrap of the fixed scroll member. The radial contact force between the orbiting and fixed scroll members is adjusted by the use of mechanical springs, or equivalent devices, to counteract some predetermined fraction of the centrifugal force exerted on the orbiting scroll member.

Turning now to FIGS. 26 and 29, the orbiting scroll is driven by the main drive shaft 250 which is mounted in the back cover plate through a bearing 251. Affixed to main drive shaft 250 is a crank 252 to which a connecting rod 253 is pivotally mounted through connecting rod pin 254. This connecting rod is affixed to the orbiting scroll member through a stub shaft 255 by means of a ball bearing 256 retained by an inner race 257 and outer race 258 (FIG. 29) mounted on ring 259 of the connecting rod. The axis of shaft 255 is designated in FIG. 29 by the numeral 260. The axis of the main shaft and of the machine is the same as that of the fixed scroll member and is therefore designated by the numeral 198. The distance between the orbiting scroll axis 260 and the machine axis 198 is $R_{or}$, the orbit radius.

Since the description of the apparatus is, for convenience, presented in terms of its serving as a compressor, main shaft 250 is shown attached to a motor 261 of a type suitable to rotate shaft 250. This motor 261 is therefore a driving means. However, it is also, as previously noted, within the scope of this invention to use this apparatus as an expansion engine, in which case the element 261 may be considered to be any suitable work absorbing means, e.g., a compressor; or a brake in the case of an expansion engine used to develop refrigeration. In these cases, the high-pressure fluid introduced into central pocket 206 is the driving means.

The swing-link, which is comprised of the connecting rod ball bearing assembly, and pin is connected to the crank through one or more springs in compression as shown in FIG. 29. A T-bolt 265 is attached to connecting rod 253 and extends through the wall of crank 252 which has a shallow well 266 on its external surface to seat concentric springs 267 and 268 held in compression by means of a spring retainer 269 adjustably affixed to T-bolt 265 by means of nut 270. Springs 267 and 268 are preloaded to a desired force through turning nut 270. The number of springs and the degree of preloading may be so chosen as to overcome a predetermined fraction of the centrifugal force exerted on the orbiting scroll member while it is achieving full running eccentricity. Thus the springs in effect pull back on the swing-link and thereby exert a centripetal force on the orbiting scroll member, the difference between the centrifugal and centripetal forces being in essence equal to the tangential sealing force. This in turn means that the tangential sealing force may be adjusted by adjusting the degree of preloading of the springs.

During start-up and shut-down (as well as periods of nonorbiting) the springs cause the swing-link to be pulled inwardly, that is toward the inner surface 271 of the crank so that the small gap 272 shown in FIG. 29 is not present. This means that the eccentricity radius of the orbiting scroll member is slightly less than the normal operating orbit radius. As the speed of the machine increases, the centrifugal force of the orbiting scroll increases, reaching a point where it balances the restraining spring force and eventually achieves a value greater than the restraining spring force. In this fashion, the initial start-up and the final portion of the shut-down operations of the machine occur without wrap-to-wrap contact of the scroll members. This in turn means that the motor 261 which turns main shaft 250 does not have to start under a load but picks up the load as the speed of the machine increases. The same desirable condition also, of course, occurs during shutdown.

As will be seen in FIG. 26, the driving mechanism also has opppositely disposed counterweights comprising a primary counterweight 273 affixed through screws 274 to the shoulder 275 of crank 252 and a secondary counterweight 276 affixed through screws 277 to a flanged extension 278 of crank 252. The counterweights are so configured with respect to size and are so positioned on the crank to eliminate vibrations in the running of the machine. It will be noted that the larger, primary counterweight 273 is positioned to exert a centrifugal force in the same direction as the centripetal force of springs 276 and 268 (FIG. 29).

In the exemplary compressor illustrated in FIG. 26, an axial loading force is applied to the orbiting scroll member 201 in the form of fluid pressure acting upon end plate surface 245. To accomplish this, a portion of the internal volume 280 defined within housing 215 is pressurized. Although it is possible to pressurize the entire volume 280, the compressor of FIG. 26 has a closure 281 within volume 280. Closure 281 is configured as a rimmed, shallow container, the rim 282 forming through a sealing ring 283 a seal with the internal wall of section 219 of housing back plate 218. A plurality of set screws 284 retain closure 281 in position and prevent its rotation. Annular ring 222 of the housing back plate serves to maintain closure 281 in alignment with crank 252 which passes through a central aperture 285 in the back wall 286 of the closure. Aperture 285 is configured to seat a wipe seal 287 contacting crank 252. Thus the volume 288 within closure 281 is isolated from volume 280 but is in fluid communication with volume 289, which is bounded by the back or external side 245 of the orbiting scroll member, through annular spacing 290 and which is isolated from the fluid pockets between the scroll members by virtue of the seal between surfaces 208 and 209.

The introduction of a high-pressure fluid, i.e., air into volume 288 through a suitable inlet line 291 thereby provides a pneumatic axial loading force acting upon the orbiting scroll member to force it toward the stationary scroll member. This means that wrap 203 of the orbiting scroll members 201 makes sealing contact along its entire length with surface 295 of stationary end plate 191 by virtue of the axial compliance/sealing characteristics of the orbiting scroll member imparted through U-shaped spring 205, thus radial sealing is attained. Likewise, wrap 192 of the stationary scroll member 190 makes sealing contact along its entire length with surface 296 of orbiting end plate 202 by virtue of the axial compliance/sealing characteristics of the stationary scroll member imparted through U-shaped spring 200. Since the U-shaped springs 205 and 200 maintain the integrity of the tangential sealing brought about through the swing-link driving mechanism, the scroll-type apparatus of this invention is highly efficient. At the same time, because of the axial compliance characteristics inherent in the construction of the scroll members and because of the radial compliance characteristics imparted through the driving mechanism all of the surfaces within the apparatus need be machined to only conventional tolerances. This fact contributes to the reduction in manufacturing costs brought about through the use of the scroll members of this invention.

It will thus be seen that the objects set forth above, among those made apparent from the preceding description, are efficiently attained and, since certain changes may be made in the above constructions without departing from the scope of the invention, it is intended that all matter contained in the above description or shown in the accompanying drawings shall be interpreted as illustrative and not in a limiting sense.

I claim:
1. A positive fluid displacement apparatus, comprising in combination
 a. a stationary scroll member formed of stationary end plate having an involute groove in one surface thereof and a separate stationary involute wrap seated in said groove in said stationary end plate;
 b. an orbiting scroll member formed of an orbiting end plate having an involute groove in one surface thereof and a separate orbiting involute wrap seated in said groove in said orbiting end plate;
 c. driving means, incorporating a main shaft and an orbiting scroll member shaft parallel therewith, for orbiting said orbiting scroll member whereby said involute wraps make moving line contacts to seal off and define at least one moving pocket of variable volume and zones of different fluid pressure on both sides of said moving line contact, said driving means including radial compliant linking means between said shaft and said orbiting scroll member shaft to attain tangential sealing along said moving line contacts;
 d. axial compliance/sealing means associated with said stationary and said orbiting wraps, whereby said stationary wrap maintains contact with the other surface of said orbiting end plate and said orbiting wrap maintains contact with the other surface of said stationary end plate;
 e. high-pressure fluid conduit means communicating with the zone of highest pressure and low-pressure fluid conduit means communicating with the zone of lowest pressure;
 f. coupling means to maintain said scroll members in fixed angular relationship; and
 g. axial force means for providing an axial force to urge said stationary involute wrap of said stationary scroll member into axial contact with said orbiting end plate of said orbiting scroll member and said orbiting involute wrap of said orbiting scroll member into axial contact with said stationary end plate of said stationary scroll member thereby in conjunction with said axial compliance/sealing means to achieve radial sealing of said pockets.

2. A positive fluid displacement apparatus in accordance with claim 1 wherein said grooves in said stationary and orbiting end plates are cut into the surfaces of said end plates.

3. A positive fluid displacement apparatus in accordance with claim 1 wherein said grooves in said stationary and orbiting end plates are defined in involute tracks on the surfaces of said end plates.

4. A positive fluid displacement apparatus in accordance with claim 1 wherein said radial compliant linking means include means to provide a centripetal radial force adapted to oppose at least a fraction of the centrifugal force acting upon said orbiting scroll member, whereby tangential sealing is attained by the radial force between said orbiting and stationary scroll members at a level to minimize both wear and internal fluid leakage.

5. A positive fluid displacement appartus in accordance with claim 1 wherein said driving means include motor means connected with said main shaft and said apparatus is a compressor.

6. A positive fluid displacement apparatus in accordance with claim 1 wherein said driving means include means to introduce high-pressure fluid into said high-pressure fluid conduit and said apparatus is an expander.

7. A positive fluid displacement apparatus in accordance with claim 1 including housing means enclosing said scroll members, said radial compliant linking means, said axial compliance/sealing means and coupling means.

8. A positive fluid displacement apparatus in accordance with claim 7 wherein said stationary end plate is affixed to said housing means through plate means defining an involute channel for circulating a cooling fluid in contact with said stationary end plate.

9. A positive fluid displacment apparatus in accordance with claim 7 wherein said axial force means comprises means to define within said housing an essentially fluid-tight chamber in part bounded by said orbiting end plate and means to introduce pressurized fluid into said chamber.

10. A positive fluid displacement apparatus in accordance with claim 1 wherein said stationary and orbiting wraps are rigidly seated in said stationary and orbiting grooves and are affixed to said stationary and orbiting end plates, respectively; wherein the contacting end surfaces of said wraps have channels therein; and wherein said axial compliance/sealing means include seal elements seated in said channels having a width which is less than the width of said channels, thus permitting said seal elements to experience small radial and axial movements, whereby said stationary and orbiting wraps maintain contact with said orbiting and stationary end plates, respectively, through said compliance/sealing means.

11. A positive fluid displacement apparatus in accordance with claim 10 wherein said axial compliance/sealing means include actuating means to actuate said seal element associated with said stationary wrap into sealing contact with said orbiting end plate and to actuate said seal element associated with said orbiting wrap into sealing contact with said stationary end plate.

12. A positive fluid displacment apparatus in accordance with claim 11 wherein said seal element actuating means comprise spring/seals.

13. A positive fluid displacement apparatus in accordance with claim 1 wherein said stationary and orbiting wraps are seated in said stationary and orbiting grooves to experience small axial and radial excursions, and said axial compliance/sealing means are positioned within said grooves, whereby said stationary and orbiting wraps maintain contact with said orbiting and stationary end plates, respectively, directly through contacting end surfaces of said stationary and orbiting wraps.

14. A positive fluid displacement apparatus in accordance with claim 13 wherein said axial compliance/sealing means comprises a plurality of spaced springs in compression.

15. A positive fluid displacement apparatus in accordance with claim 13 wherein said axial compliance/sealing means comprises elastomeric extending throughout the lengths of said involutely configured grooves.

16. A positive fluid displacment apparatus in accordance with claim 13 wherein said axial compliance/sealing means comprise involutely configured spring/seals extending throughout the lengths of said involutely configured grooves.

17. A positive fluid displacment apparatus in accordance with claim 13 including auxiliary axial compliance/sealing means associated with said stationary and orbiting wrap contacting end surfaces.

18. A set of complementary scroll members for use in scroll-type apparatus for defining moving fluid pockets and zones of different fluid pressure within said apparatus, comprising in combination
  a. a first scroll member comprising
   1. a first end plate having on the one of its surfaces serving as one of the boundaries for said fluid pockets a first involutely configured groove, and
   2. a separate first involute wrap having a first contacting end surface, being involutely configured to conform to the configuration of said first groove, and being located in said first groove, the width of at least the first wrap position in said first groove being less than the width of said first groove to permit said first wrap to experience small radial and axial excursions in said first groove;
  b. a second scroll member comprising
   3. a second end plate having on the one of its surfaces serving as another of the boundaries for said fluid pockets a second involutely configured groove, and
   4. a separate second involute wrap having a second contacting end surface, being involutely configured to conform to the configuration of said second groove, and being located in said second groove, the width of at least the second wrap portion in said second groove being less than the width of said second groove to permit said second wrap to experience small radial and axial excursions in said second groove;
  c. first force applying means associated with said first wrap and located in said first groove for applying an axial force on said first wrap, whereby said first contracting end surface of said first wrap maintains contact with said second end plate; and
  d. second force applying means associated with said second wrap and located in said second groove for applying an axial force on said second wrap, whereby said second contacting end surface of said second wrap maintains contact with said first end plate.

19. A set of complementary scroll members in accordance with claim 18 wherein said first and second force applying means comprise a plurality of spaced springs in compression in axial force applying relationship to said first and second wraps.

20. A set of complementary scroll members in accordance with claim 18 wherein said first and second force applying means comprise elastomeric members extending throughout the lengths of said first and second involutely configured grooves.

21. A set of complementary scroll members in accordance with claim 18 wherein said first and second force applying means comprise involutely configured spring/seals extending throughout the lengths of said first and second involutely configured grooves.

22. A set of complementary scroll members in accordance with claim 18 wherein said first and second contacting end surfaces of said first and second wraps each has a channel following the configuration of its wrap, and including first and second axial compliance/sealing means associated with said first and second contacting end surfaces, each of said axial compliance/sealing means comprising in combination a seal element of the same involute configuration as said channel, seated in said channel and having a width which is less than the width of said channel to permit said seal element to experience small radial and axial excursions within said channel, said seal element having a contacting surface width less than that which said wrap would have in the absence of said compliance/sealing means; and seal element force applying means for actuating said seal element to effect axial contact.

23. A set of complementary scroll members for use in scroll-type apparatus for defining moving fluid pockets and zones of different fluid pressures within said apparatus, comprising in combination.
  a. a first scroll member comprising
    1. a first end plate having on the one of its surfaces serving as one of the boundaries for said fluid pockets a firsst involutely configured groove, and
    2. a separate first involute wrap rigidly seated in said first groove and having a first contacting end surfaces with a first channel defined therein, said first wrap being involutely configured to conform to the configuration of said first groove;
  b. a second scroll member comprising
    3. a second end plate having on the one of its surfaces serving as another of the boundaries for said fluid pockets a second involutely configured groove, and
    4. a separate second involute wrap rigidly seated in said second groove and having a second contacting end surface with a second channel defined therein, said second wrap being involutely configured to conform to the configuration of said second groove;
  c. first and second axial compliance/sealing means associated with said first and second wraps, respectively, each of said axial compliance/sealing means comprising in combination a seal element of the same involute configuration as said channel, seated in said channel and having a width which is less than the width of said channel to permit it to experience small radial and axial excursions within said channel, said seal element having a contacting surface width less than the contacting surface width which said wrap would have in the absence of said compliance/sealing means; and force applying means for actuating said seal element to effect said axial contact while maintaining the integrity of said tangential sealing during operation of said apparatus.

24. A set of complementary scroll members in accordance with claim 23 wherein said force applying means of said first and second axial compliance/sealing means comprise a plurality of spaced springs in compression in axial force applying relationship to said seal elements.

25. A set of complementary scroll members in accordance with claim 23 wherein said force applying means of said first and second axial compliance/sealing means comprise elastromeric members extending throughout the lengths of said first and second involutely configured channels.

26. A set of complementary scroll members in accordance with claim 23 wherein said force applying means of said first and second axial compliance/sealing means comprise involutely configured spring/seals extending throughout the lengths of said first and second involutely configured channels.

* * * * *